US010918826B2

(12) United States Patent
Shorey (10) Patent No.: US 10,918,826 B2
(45) Date of Patent: Feb. 16, 2021

(54) COAXIAL VENAL CANNULA (71) Applicant: NORDSON CORPORATION, Westlake, OH (US)

(72) Inventor: Frederick A. Shorey, East Grand Rapids, MI (US)

(73) Assignee: Nordson Corporation, Westlake, OH (US)

( * ) Notice: Subject to any disclaimer, the term of this patent is extended or adjusted under 35 U.S.C. 154(b) by 503 days.

(21) Appl. No.: 15/805,376

(22) Filed: Nov. 7, 2017

(65) Prior Publication Data

US 2018/0085553 A1 Mar. 29, 2018

Related U.S. Application Data

(62) Division of application No. 14/967,282, filed on Dec. 12, 2015, now Pat. No. 9,925,353, which is a division
(Continued)

(51) Int. Cl.
*A61M 25/00* (2006.01)
*A61M 1/36* (2006.01)
(Continued)

(52) U.S. Cl.
CPC ...... *A61M 25/0026* (2013.01); *A61M 25/005* (2013.01); *A61M 25/0029* (2013.01);
(Continued)

(58) Field of Classification Search
CPC .......... A61M 25/0026; A61M 25/0029; A61M 25/0043; A61M 25/005; A61M 25/0069; A61M 25/0097; A61M 25/007; A16M 1/3659; A16M 1/1698; A16M 1/3653; A16M 2025/0004; A16M 2025/0031;
(Continued)

(56) References Cited

U.S. PATENT DOCUMENTS 3,630,207 A 12/1971 Kahn et al.
4,037,599 A 7/1977 Raulerson
(Continued)

FOREIGN PATENT DOCUMENTS

EP 1649889 A1 4/2006
WO 00/25849 A1 5/2000

*Primary Examiner* — David P Bryant
*Assistant Examiner* — Nirvana Deonauth
(74) *Attorney, Agent, or Firm* — Baker & Hostetler LLP (57) ABSTRACT

A dual lumen cannula includes a first tube defining a return lumen and having a proximal end, a mid-portion and a distal end, wherein the distal end includes a return aperture. A second tube is coaxial with the first tube and has a proximal end and a distal end, wherein the distal end of the second tube is fixedly attached to the mid-portion of the first tube and wherein the distal end of the second tube includes a drainage aperture. A drainage lumen is defined by a space between the first tube and the second tube. A connector is attached to the proximal end of the second tube. The connector includes a reservoir for receiving a fluid from the proximal end of the second tube. The first tube extends through the connector and does not attach directly with the second tube at the connector, and the first tube remains substantially coaxial with the second tube throughout a length of the second tube.

20 Claims, 10 Drawing Sheets

Related U.S. Application Data of application No. 12/145,738, filed on Jun. 25, 2008, now Pat. No. 9,233,223.

(60) Provisional application No. 60/946,277, filed on Jun. 26, 2007.

(51) Int. Cl.
*A61M 39/10* (2006.01)
*A61M 1/16* (2006.01)

(52) U.S. Cl.
CPC .... *A61M 25/0043* (2013.01); *A61M 25/0069* (2013.01); *A61M 25/0097* (2013.01); *A61M 1/1698* (2013.01); *A61M 1/3653* (2013.01); *A61M 1/3659* (2014.02); *A61M 25/007* (2013.01); *A61M 2025/0004* (2013.01); *A61M 2025/0031* (2013.01); *A61M 2025/0039* (2013.01); *A61M 2039/1077* (2013.01); *A61M 2039/1088* (2013.01); *A61M 2207/00* (2013.01); *Y10T 29/49947* (2015.01)

(58) Field of Classification Search
CPC ...... A16M 25/0039; A16M 2039/1077; A16M 2039/1088; A16M 2207/00; Y10T 29/49947
See application file for complete search history.

(56) References Cited

U.S. PATENT DOCUMENTS

| | | | |
|---|---|---|---|
| 4,270,535 A | 6/1981 | Bogue et al. |
| 4,493,595 A | 1/1985 | Klein |
| 4,493,696 A | 1/1985 | Uldall |
| 4,543,597 A | 9/1985 | Shibata |
| 4,547,193 A | 10/1985 | Rydell |
| 4,548,597 A | 10/1985 | Nelson |
| 4,639,252 A | 1/1987 | Kelly et al. |
| 4,666,426 A | 5/1987 | Aigner |
| 4,950,257 A | 8/1990 | Hibbs et al. |
| 4,979,942 A | 12/1990 | Wolf et al. |
| 5,009,636 A | 4/1991 | Wortley et al. |
| 5,053,004 A | 10/1991 | Markel et al. |
| 5,066,285 A | 11/1991 | Hillstead |
| 5,209,723 A | 5/1993 | Twardowski et al. |
| 5,312,355 A | 5/1994 | Lee |
| 5,324,253 A | 6/1994 | McRea et al. |
| 5,346,471 A | 9/1994 | Raulerson |
| 5,350,358 A | 9/1994 | Martin |
| 5,395,341 A | 3/1995 | Slater |
| 5,405,320 A | 4/1995 | Twardowski et al. |
| 5,454,997 A | 10/1995 | Karlin et al. |
| 5,472,435 A | 12/1995 | Sutton |
| 5,480,380 A | 1/1996 | Martin |
| 5,531,719 A | 7/1996 | Takahashi |
| 5,536,261 A | 7/1996 | Stevens |
| 5,718,678 A | 2/1998 | Fleming, III |
| 5,766,151 A | 6/1998 | Valley et al. |
| 5,769,828 A | 6/1998 | Jonkman |
| 5,797,869 A | 8/1998 | Martin et al. |
| 5,800,409 A | 9/1998 | Bruce |
| 5,873,854 A | 2/1999 | Wolvek |
| 5,938,587 A | 8/1999 | Taylor et al. |
| 5,947,940 A | 9/1999 | Beisel |
| 5,959,379 A | 9/1999 | Hu et al. |
| 5,961,485 A | 10/1999 | Martin |
| 5,976,103 A | 11/1999 | Martin |
| 5,989,206 A | 11/1999 | Prosl et al. |
| 6,001,056 A | 12/1999 | Jassawalla et al. |
| 6,007,478 A | 12/1999 | Siess et al. |
| 6,083,260 A | 7/2000 | Aboul-Hosn |
| 6,110,139 A | 8/2000 | Loubser |
| 6,113,568 A | 9/2000 | Olaussen |
| 6,123,725 A | 9/2000 | Aboul-Hosn |
| 6,190,393 B1 | 2/2001 | Bevier et al. |
| 6,358,238 B1 | 3/2002 | Sherry |
| 6,383,172 B1 | 5/2002 | Barbut |
| 6,454,997 B1 | 9/2002 | Divino et al. |
| 6,533,770 B1 | 3/2003 | Lepulu et al. |
| 6,582,388 B1 | 6/2003 | Coleman et al. |
| 6,589,227 B2 | 7/2003 | Soenderskov |
| 6,596,235 B2 | 7/2003 | Divino et al. |
| 6,602,468 B2 | 8/2003 | Patterson et al. |
| 6,620,118 B1 | 9/2003 | Prosl et al. |
| 6,652,492 B1 | 11/2003 | Bell et al. |
| 6,673,039 B1 | 1/2004 | Bridges et al. |
| 6,682,498 B2 | 1/2004 | Ross |
| 6,692,473 B2 | 2/2004 | Cyr St et al. |
| 6,743,219 B1 | 6/2004 | Dwyer et al. |
| 6,759,008 B1 | 7/2004 | Patterson et al. |
| 6,858,001 B1 | 2/2005 | Aboul-Hosn |
| 6,942,635 B2 | 9/2005 | Rosenblatt et al. |
| 6,969,379 B1 * | 11/2005 | Aboul-Hosn ....... A61M 1/3666 128/898 |
| 6,974,436 B1 | 12/2005 | Aboul-Hosn et al. |
| 6,976,979 B2 | 12/2005 | Lawrence et al. |
| 7,135,008 B2 | 11/2006 | O'Mahony et al. |
| 2001/0001812 A1 | 5/2001 | Valley et al. |
| 2002/0165600 A1 | 11/2002 | Banas et al. |
| 2003/0078564 A1 | 4/2003 | Viitala |
| 2003/0097114 A1 | 5/2003 | Ouriel et al. |
| 2004/0210180 A1 | 10/2004 | Altman |
| 2005/0004504 A1 | 1/2005 | Frye et al. |
| 2005/0070878 A1 | 3/2005 | Triplett et al. |
| 2005/0080398 A1 | 4/2005 | Markel et al. |
| 2005/0085761 A1 | 4/2005 | Wang et al. |
| 2005/0228212 A1 | 10/2005 | Aboul-Hosn et al. |
| 2005/0279370 A1 | 12/2005 | Aboul-Hosn et al. |
| 2006/0089618 A1 | 4/2006 | McFerran et al. |
| 2006/0100565 A1 | 5/2006 | Aboul-Hosn |
| 2007/0049902 A1 | 3/2007 | Griffin et al. |
| 2009/0062735 A1 | 3/2009 | Bartlett et al. |
| 2009/0076482 A1 | 3/2009 | Jonkman |

* cited by examiner

COAXIAL VENAL CANNULA

CROSS REFERENCE TO RELATED APPLICATION

This application is a divisional of U.S. patent application Ser. No. 14/967,282, filed Dec. 12, 2015, and published as U.S. Patent App. Pub. No. 2016/0095972 on Apr. 7, 2016, which is a divisional of U.S. patent application Ser. No. 12/145,738, filed Jun. 25, 2008, and issued as U.S. Pat. No. 9,233,223 on Jan. 12, 2016, which claims the benefit of U.S. Provisional Patent App. No. 60/946,277, filed Jun. 26, 2007. This application is also related to U.S. patent application Ser. No. 12/145,763, filed Jun. 25, 2008, and published as U.S. Patent App. Pub. No. 2009/0062735 on Mar. 5, 2009, and to U.S. patent application Ser. No. 12/145,798, filed Jun. 25, 2008, and issued as U.S. Pat. No. 8,377,036 on Feb. 19, 2013. The entire contents of each of the aforementioned applications is incorporated herein by reference.

BACKGROUND OF THE PRESENT INVENTION

In the past, in long term life support cases or long term extracorporeal support cases, it has been difficult to justify the use of an external blood circuit where a ventilator can be used. However, in cases where ventilators are used, there can be major complications and risks associated with the use of a tracheal tube and artificial lung inflation. Artificial ventilation oftentimes has negative effects including ventilator dependency and permanent scarring.

Currently, extracorporeal membrane oxygenation ("ECMO") is used with neonatal and pediatric patients because ventilator use is not preferred. Current dual lumen cannulae for ECMO or blood circuit support cannot be used on adults because of sizing constraints, because these cannulae have a tendency to kink, and because they can cause blood damage. The cannulae are inserted generally in one location and are restricted in their placement depth. Traditional cannulae used for adult life support generally involve single lumen cannulae at multiple insertion sites, high volume circuits and cannulae that are not capable of long term use. Multiple sites increase the risk of bleeding, vessel damage, infection, as well as pain and discomfort to the patient. These cannulae are designed and built for short term acute therapies.

Therefore, a cannula that has multiple uses, includes one insertion site and can be used for long term applications would be beneficial.

SUMMARY OF THE INVENTION

One aspect of the present invention includes a dual lumen cannula assembly having an infusion tube defining a return lumen and having a first outer circumference, a proximal end, and a distal end that includes a return aperture. A drainage tube is co-axially aligned with the infusion tube and has a second outer circumference, a proximal end and a distal end. The distal end of the drainage tube includes a drainage site having a drainage aperture and wherein the length of the drainage tube is less than the length of the infusion tube. A drainage lumen is defined by a space between the infusion tube and the drainage tube. A connector is attached to the proximal end of the drainage tube and has a reservoir for receiving fluid from the proximal end of the drainage tube, wherein the infusion tube extends through the connector and does not attach with the drainage tube at the connector, and further wherein the infusion tube remains substantially coaxial with the drainage tube throughout the length of the drainage tube.

Another aspect of the present invention includes a dual lumen cannula assembly having an infusion tube with a distal end and a proximal end, and a drainage tube with a distal end and a proximal end. The drainage tube is co-axially aligned with the infusion tube. An improvement includes a connector having a reservoir, a connector aperture that is fluidly connected to a mouth on a proximal end of the drainage tube, and a return opening on the connector, wherein the outside circumference of the infusion tube is attached to the return opening. A drainage member is connected to the distal end of the drainage tube and further connected to the outside circumference of the first small tube between the proximal and distal ends of the small tube, the drainage member including at least one drainage aperture. A return aperture is disposed adjacent to the distal end of the infusion tube.

Yet another aspect of the present invention includes a method of making a cannula assembly by forming an elongate flexible infusion tube having a proximal end and a distal end. An elongate flexible drainage tube is formed having a proximal end and a distal end. A connector is formed that has a return opening and a connector aperture. The elongate infusion tube is inserted into the return opening and out the connector aperture. The infusion tube is attached to the return opening of the connector. The distal end of the elongate return tube is connected to a mid-portion of the elongate infusion tube. A drainage site having at least one drainage aperture is installed at the distal end of the elongate return tube. An infusion site having at least one infusion aperture is installed at the distal end of the elongate infusion tube.

In another aspect of the present invention, the inside tube passes through the connector and is not connected internally therewith, thereby providing a smooth, seamless transition from the blood return line to the return aperture. Because there are no internal bond joints, welds, or connections throughout the entire extent of the return lumen, the blood that is returned to the patient's body from an ECMO circuit is delivered without risk of damage from potential irregularities formed by internal bond joints, welds or other forms of connection.

These and other features, advantages and objects of the present invention will be further understood and appreciated by those skilled in the art upon studying the following specification, claims, and appended drawings.

DETAILED DESCRIPTION OF PREFERRED EMBODIMENTS

Figure 1:
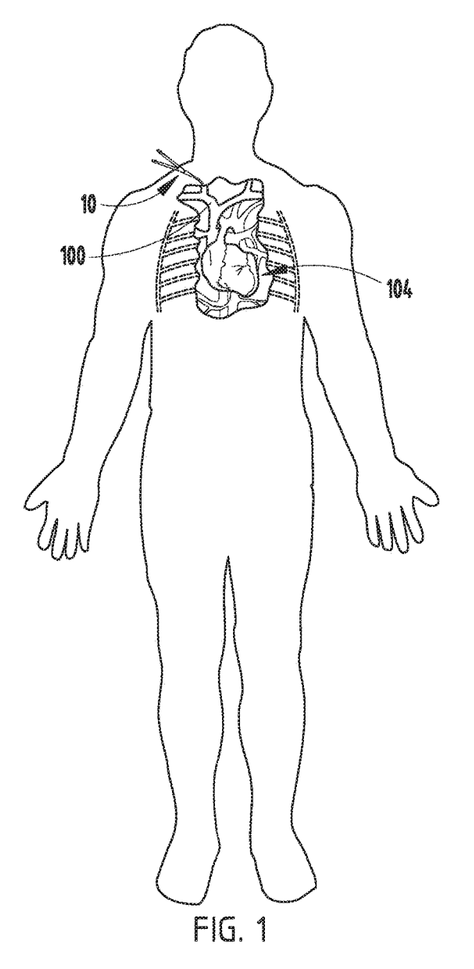
FIG. 1 is a top elevational view of one embodiment of a coaxial cannula of the present invention inserted into the body of a patient.

For purposes of description herein the terms "upper", "lower", "right", "left", "rear", "front", "vertical", "horizontal" and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 2:
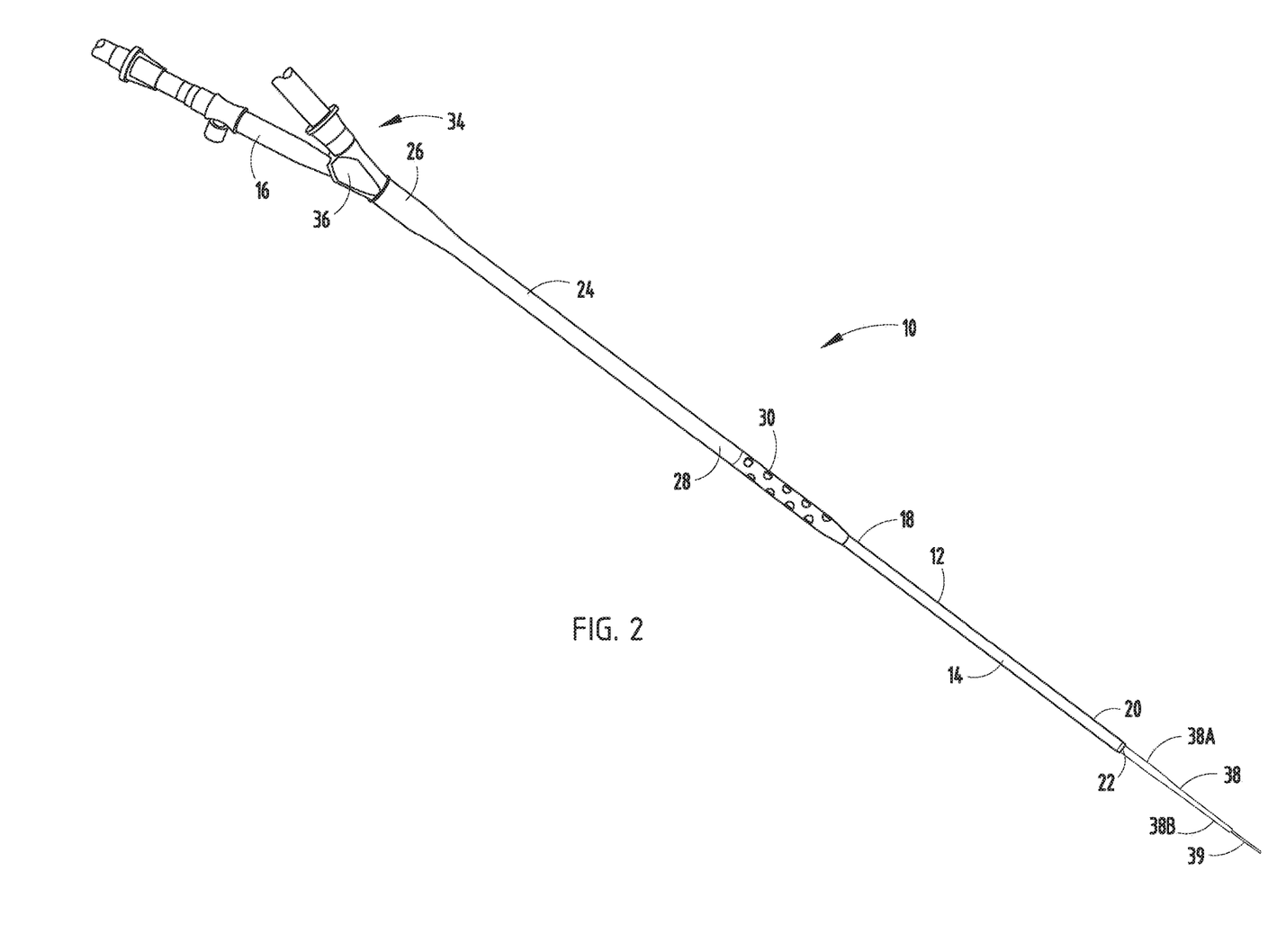
FIG. 2 is a top perspective view of one embodiment of a coaxial cannula of the present invention.
Figures 3, 4, 5:
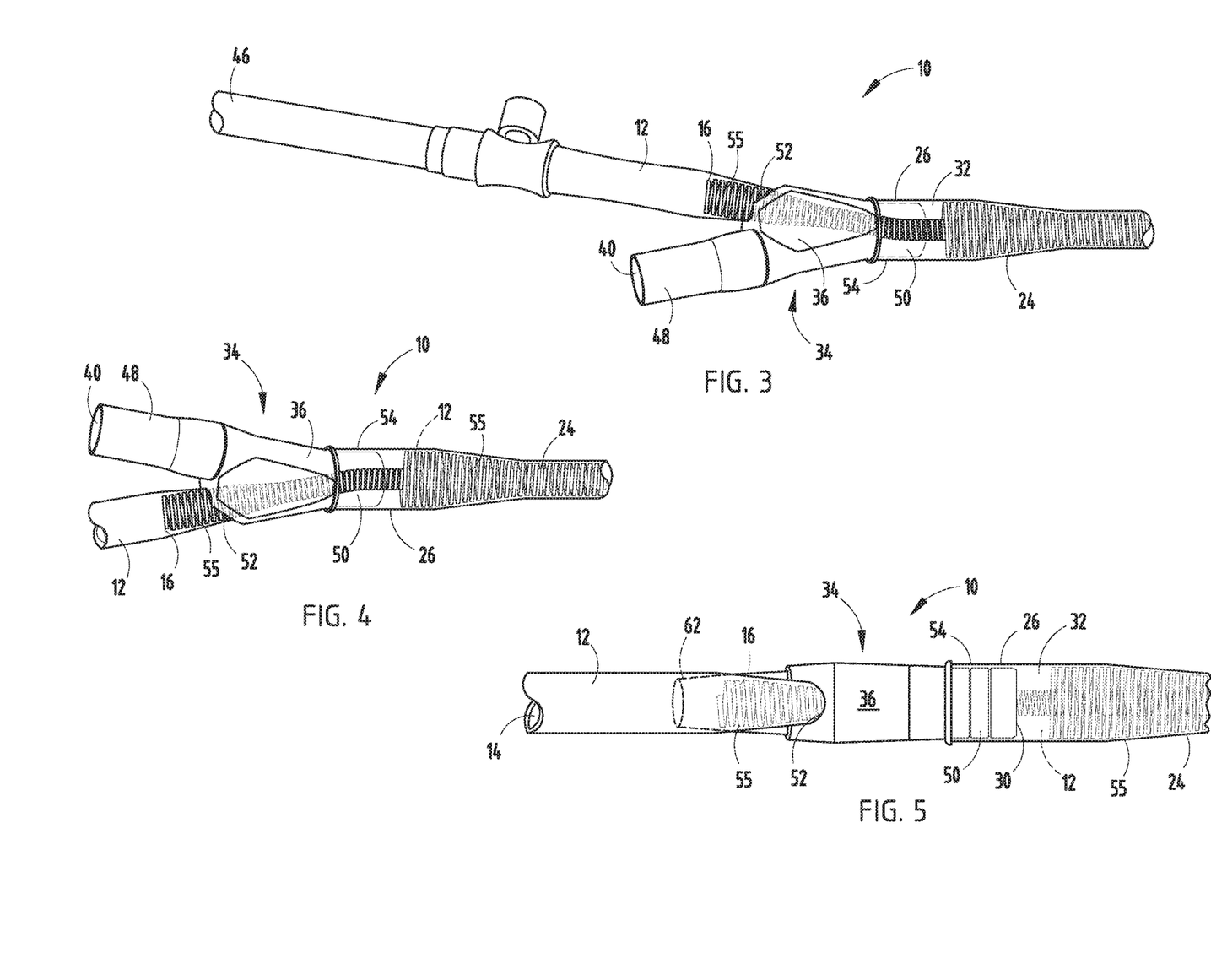
FIG. 3 is a partial enlarged top perspective view of a rear portion of the coaxial cannula of FIG. 2.
FIG. 4 is a partial enlarged bottom perspective view of the rear portion of the coaxial cannula of FIG. 2.
FIG. 5 is a partial enlarged side elevational view of the rear portion of the coaxial cannula of FIG. 2.

The reference numeral 10 shown in FIGS. 1-3 generally designates a dual lumen cannula that includes a first infusion tube 12 having an outside circumference and defining an internal or return lumen 14. The first infusion tube 12 includes a proximal end 16, a mid-portion 18 and a distal end 20, wherein the distal end 20 includes a return aperture 22. A second drainage tube 24 is coaxial with the first tube 12 and has a proximal end 26 and a distal end 28, wherein the distal end 28 of the second tube 24 is fixedly attached to the mid-portion 18 of the first tube 12 and wherein the distal end 28 is adjacent a drainage aperture 30. An external or drainage lumen 32 (FIG. 3) is defined between the first tube 12 and the second tube 24. A connector 34 is attached to the proximal end 26 of the second tube 24, and the connector 34 includes a reservoir 36 for receiving fluid from the proximal end 26 of the second tube 24, wherein the first tube 12 extends through the connector 34 and does not connect with the second tube 24 at the connector 34, and wherein the first tube 12 remains substantially coaxial with the second tube 24 throughout the length of the second tube 24.

Figure 20:
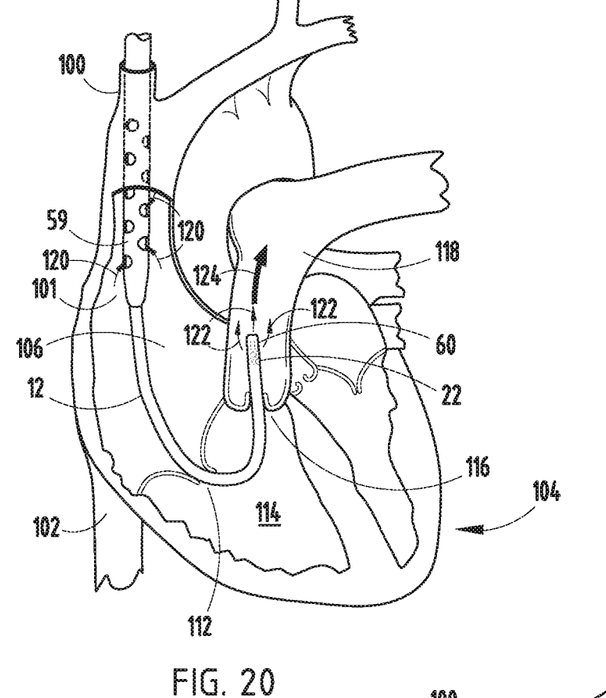
FIG. 20 is a front elevational view of a coaxial cannula of the instant invention inserted through the superior vena cava and into the heart.
Figure 21:
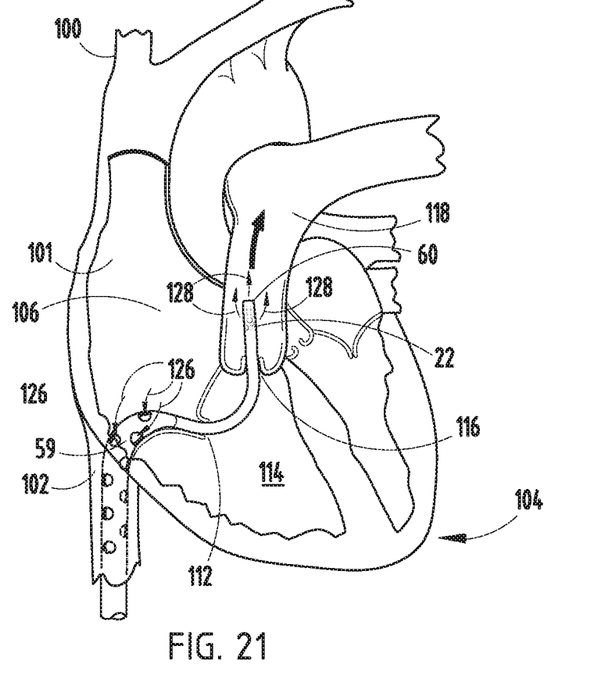
FIG. 21 is a front elevational view of a coaxial cannula of the instant invention inserted through the inferior vena cava and into the heart.

Referring again to FIGS. 1 and 2, the extracorporeal support cannula 10 has substantial placement flexibility that allows the extracorporeal support cannula 10 to be placed in a patient at various vascular insertion sites and depths. The extracorporeal support cannula 10 is designed for placement above or below the right atrium and therefore will not typically cross the heart as disclosed below with reference to FIGS. 1, 18 and 19. Accordingly, the extracorporeal support cannula 10 is less intrusive than cannulae that cross the heart. However, the extracorporeal support cannula 10 can be used to cross the heart in certain applications, as shown in FIGS. 20 and 21. The extracorporeal support cannula 10 is adapted for use with an introducer 38 (FIG. 1) that extends through the cannula and helps the user to properly place the extracorporeal support cannula 10 in the correct position and depth in the body of a patient. The introducer 38 may include a transition portion 38A and extended portion 38B and a guide wire 39 extending therethrough. Various introducers, such as described in related application Ser. No. 12/145,763, entitled INTRODUCER FOR CANNULA AND METHOD, which is incorporated herein in its entirety, can be used with the extracorporeal support cannula 10. The first or inside tube 12 and second or outside tube 24 are made from polyurethane, but could also be made from PVC or silicone, and are dip molded, or extruded. Optionally, the tubes 12, 24 may be extruded and dip coated during construction.

Referring now to FIGS. 3-5, the illustrated connector 34 includes a connector aperture 50 that is connected to the proximal end 26 of the outside tube 24. Connector 34 also includes a return opening 52 through which an inside tube 12 extends and the drainage opening 40, which is aligned with and connected to a drainage line 48. The connector aperture 50 of the connector 34 is attached with a mouth 54 at the proximal end 26 of the outside tube 24 and may be glued or welded thereto. The outside tube 24 is reinforced with a stainless steel coil 55 that wraps circumferentially about the outside tube 24 to minimize kinking or collapse of the extracorporeal support cannula 10. The mouth 54 of the outside tube 24 has a larger diameter than the remainder of the outside tube 24. This design slows down the speed of blood flow inside the cannula 10 prior to the blood reaching the ECMO apparatus, which minimizes damage to the blood.

Figure 7:
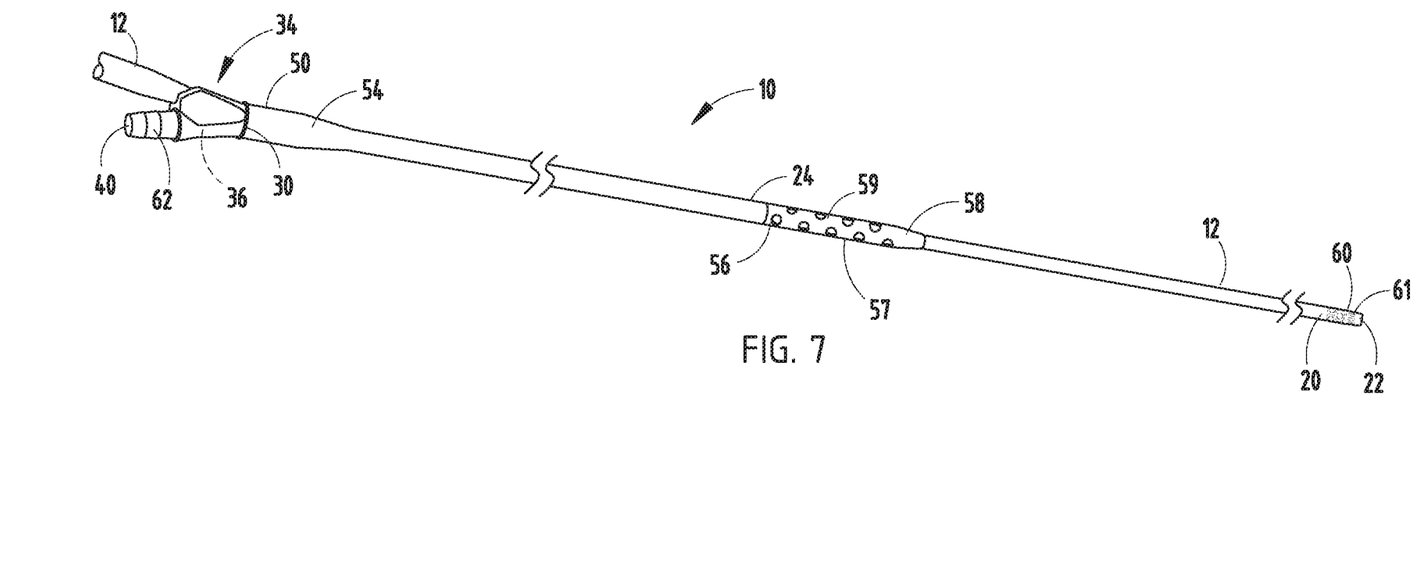
FIG. 7 is a top perspective view of the rear portion of the coaxial cannula of FIG. 6.
Figure 12:
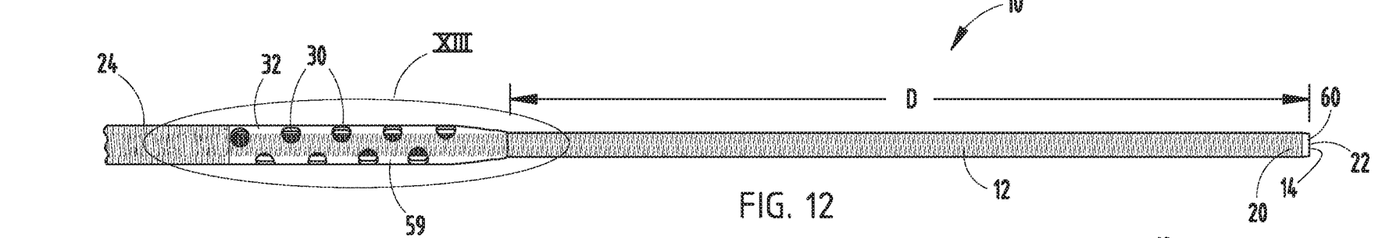
FIG. 12 is a top elevational view of one embodiment of a front portion of a coaxial cannula of the instant invention.
Figure 13:
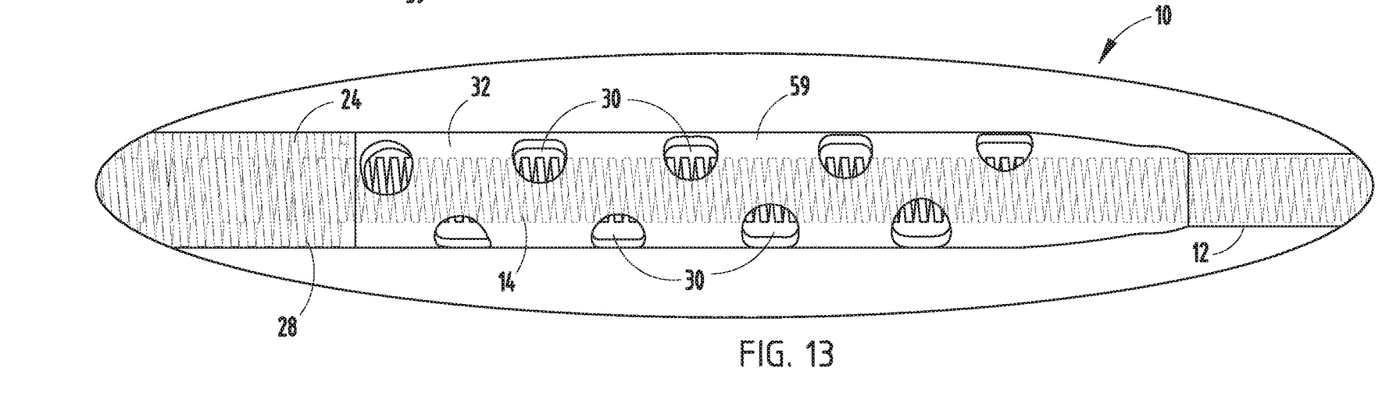
FIG. 13 is a top elevational view of a portion of the coaxial cannula of FIG. 12 taken at XIII.

As shown in FIGS. 7 and 12, the distal end 28 of the outside tube 24 is bonded to the outside circumference of the inside tube 12 adjacent to a drainage site 59. The inside and outside tubes 12, 24 may directly connect adjacent the blood drainage site 59. Alternatively, the distal end 28 of the outside tube 24 may connect to a rearward end 56 of a separate stiffened drainage member 57, while a forward end 58 of the drainage member 57 connects to the outside circumference of the inside tube 12. The drainage member 57 smoothly transitions the outside circumference of the inside tube 12 to the outside circumference of the outside tube 24. The inside tube 12 extends beyond the outer tube 24 and terminates proximate a blood return site 60 (FIGS. 7 and 12). The blood return site 60 may include an infusion basket 61. Baskets for use in drainage and infusion of blood and which are designed for use in the extracorporeal support cannula 10 are disclosed in further detail in related application Ser. No. 12/145,798, entitled CANNULA REIN- FORCING BAND AND METHOD, which is incorporated by reference herein in its entirety.

Figure 6:
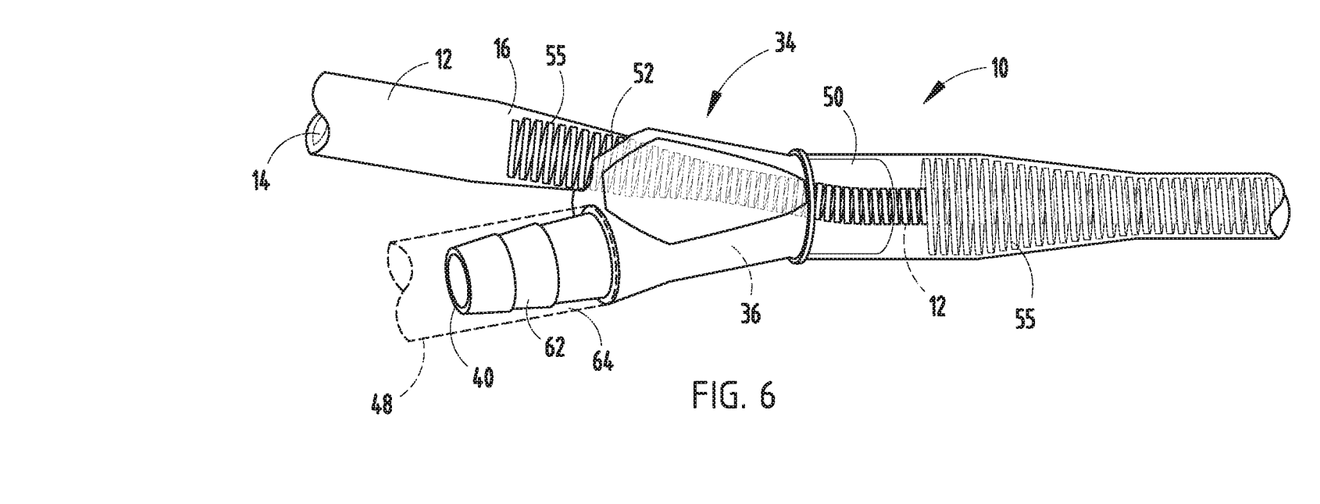
FIG. 6 is an enlarged top elevational view of the rear portion of another embodiment of a coaxial cannula of the present invention.

Referring now to FIGS. 6 and 7, the illustrated embodiment shows the connector 34 having a male extension portion 62. The male extension portion 62 is adapted for insertion into a female end 64 of the drainage line 48 to allow deoxygenated blood to flow from the body of a patient, through the reservoir 36 of the connector 34 to the drainage line 48 for oxygenation in an ECMO apparatus.

Figure 8:
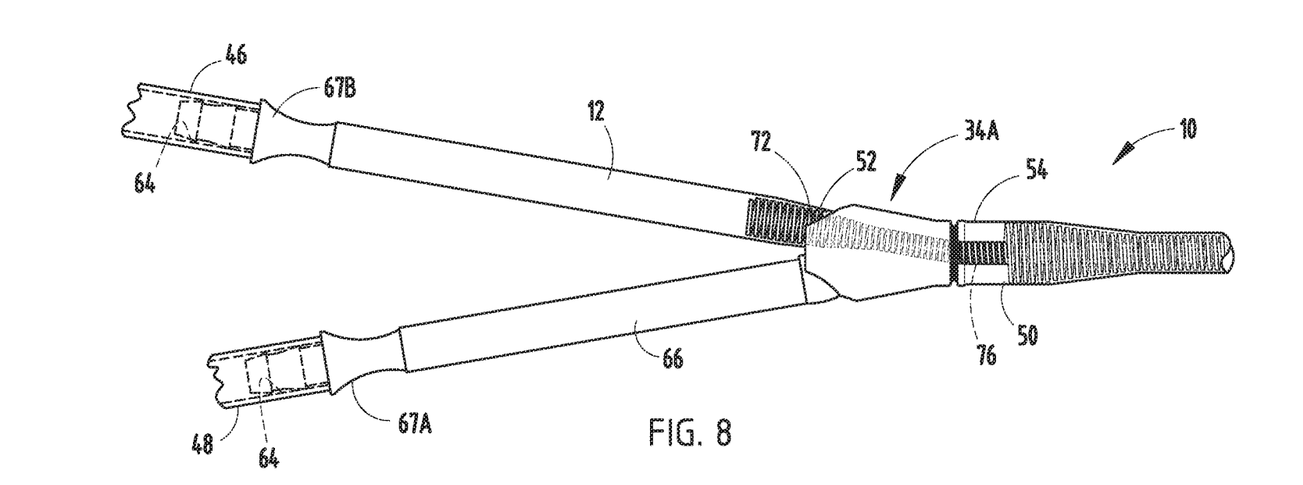
FIG. 8 is an enlarged top elevational view of the rear portion of another embodiment of a connector of a coaxial cannula of the present invention.
Figure 9:
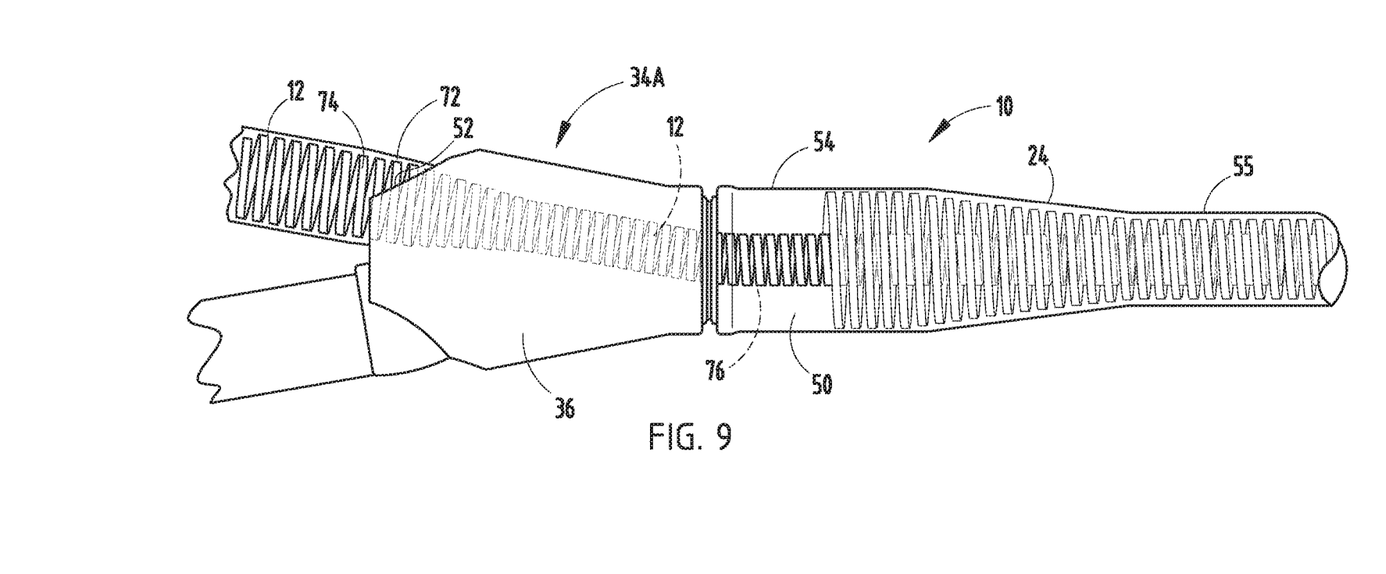
FIG. 9 is an enlarged elevational view of the rear portion of the coaxial cannula of FIG. 8.
Figures 10, 11:
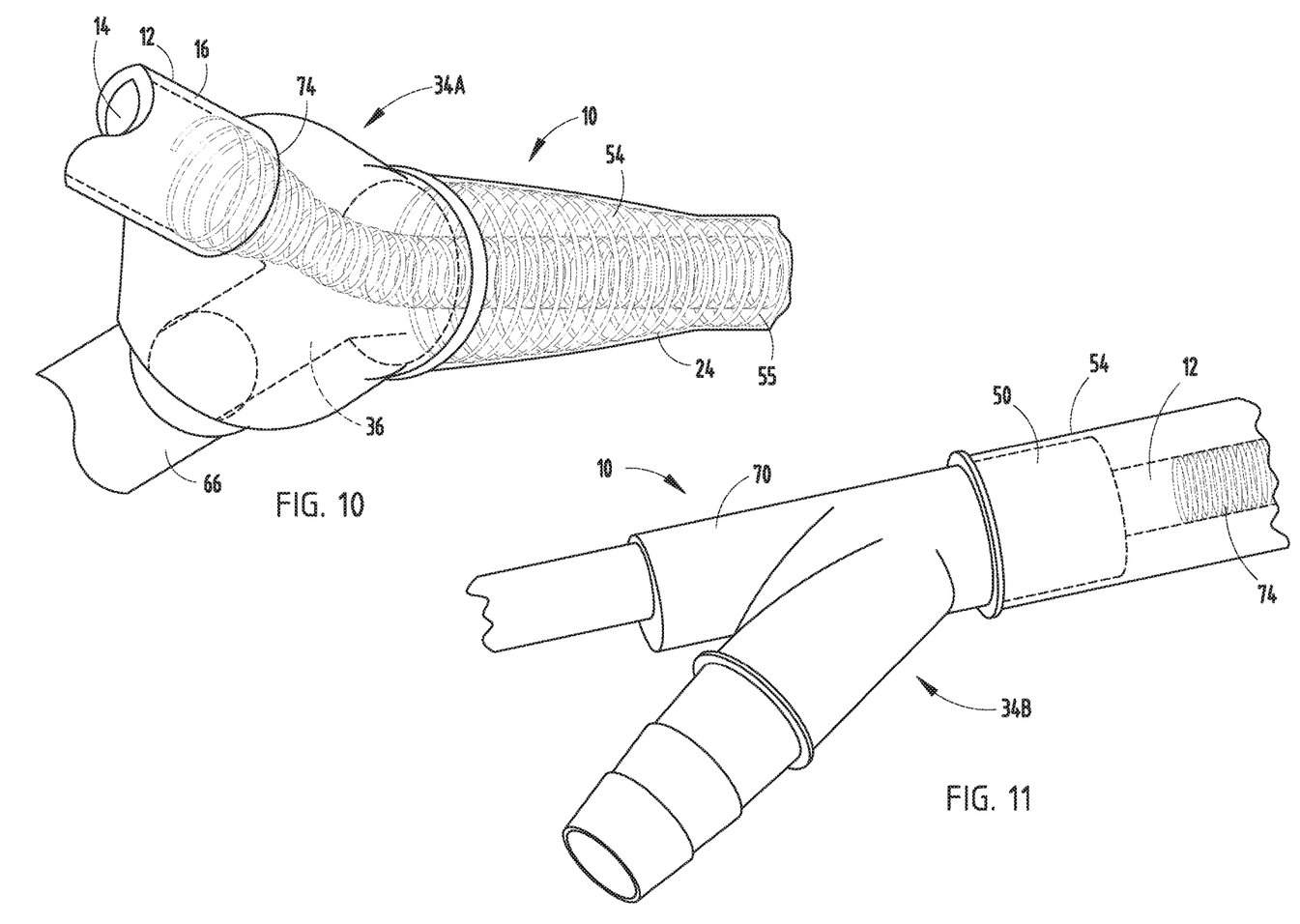
FIG. 10 is an enlarged rear perspective view of a coaxial cannula.
FIG. 11 is a top perspective view of the rear portion of another embodiment of a connector of the instant invention.

The illustrated embodiment shown in FIGS. 8-10 illustrates an alternative connector 34A that includes a bridge tube 66 that attaches the connector 34A to a drainage junction 67A which is adapted for insertion into the female end 64 of the drainage line 48. As illustrated, the bridge tube 66 is inserted into the connector 34A and secured to the inside of the connector 34A by adhesive or an interference fit. The inside tube 12 extends through the connector 34A and terminates at a drainage junction 67B which is adapted for insertion into a female end 64 of the blood return line 46.

The illustrated example of FIG. 11 shows a connector 34B which has a similar construction to connectors 34 and 34A outlined above, but also including an infusion extension portion 70. The infusion extension portion 70 provides structural rigidity to the inside tube 12 as the inside tube 12 extends through the connector 34B. This arrangement minimizes the likelihood of kinking at the point where the inside tube 12 extends from the connector 34B before connecting with the return line 46.

Referring to FIGS. 4-12, in each of the illustrated examples, the inside tube 12 passes through the connector 34, 34A, or 34B thereby providing a smooth, seamless transition from the blood return line 46 to the return opening 52. Joints, weldments and other connections can create irregularities in the flow of blood and can damage blood cells. Because there are no internal bond joints, welds, or connections throughout the entire extent of the return lumen 14, the blood that is returned to a patient's body from an ECMO apparatus is delivered without risk of damage from potential irregularities formed by internal bond joints, welds or other forms of connection.

The connectors 34, 34A and 34B disclosed above with respect to FIGS. 6-12 are generally made from polycarbonate, but could also be made from PVC, acrylic, or polyurethane. The connectors 34, 34A and 34B are constructed using an operation including injection molding, machining or dip forming.

Referring again to FIGS. 7-9, the proximal end 16 of the inside tube 12 receives oxygenated blood from an oxygenator (not shown) and sends it through a transition portion 72 (FIG. 9) that is tapered and reinforced with a stainless steel coil 74 that wraps circumferentially about the inside tube 12. The coil 74 as well as the coil 55 of the outside tube 24 may also be made from nitinol or plastic. As the proximal end 16 of the inside tube 12 tapers, it enters into the return opening 52 of connector 34 and extends therethrough thus allowing the return lumen 14 of inside tube 12 to be continuous and without bonds or joints through the connector 34. Depending on the application, the inside tube 12 may or may not include structural reinforcement in a middle section 76 of the inside tube 12. If the middle section 76 is not reinforced, the inside tube 12 can have a thinner wall construction and consequently better flow characteristics. The unreinforced middle section 76 of the inside tube 12 transitions to the distal end 20 at a blood return site 60 which may be reinforced by the coil 74. Alternatively, if the middle section 76 of the inside tube 12 is reinforced, then the inside tube 12 is stronger and less susceptible to kinking or collapse of the inside tube 12.

Referring now to FIGS. 12-16, the illustrated example shows the inside tube 12 of the extracorporeal support cannula 10, which defines the internal lumen 14. Also, as disclosed above, the external lumen 32 extends through the extracorporeal support cannula 10 and is defined by the space between the inside tube 12 and the outside tube 24. The function of the internal lumen 14 is to deliver oxygenated blood to the bloodstream of a patient at a return site 60 that includes at least one return aperture 22. The return site 60 is located at the distal end 20 of the inside tube 12. The function of the external lumen 32 is to drain blood from the bloodstream of a patient through the drainage site 59. The drainage site 59 includes multiple drainage apertures 30 that extend orthogonal to the longitudinal extent of the outside tube 24. It is contemplated that the apertures 30 could extend at an angle relative to the outside tube 24 and that various arrangements of drainage apertures 30 could be utilized. For example, extended drainage could be incorporated wherein the drainage apertures 30 extend continuously along the longitudinal extent of the outside tube 24. Alternatively, the drainage apertures 30 could be grouped into a multi-site arrangement wherein several groups of drainage apertures 30 are present along the longitudinal extent of the outside tube 24. Advantages to these arrangements include a shorter flow path through the ECMO circuit as well as a lower pressure drop at the drainage site(s) 59 (the more drainage apertures 30, the lower the pressure on the blood). It is contemplated that the drainage apertures 30 could be oriented in any of the arrangements outlined above, as well as others. The drainage site 59 may be located at the distal end 28 of the outside tube 24 adjacent the mid-portion 18 of the first tube 12 or close to the distal end 20 of the inside tube 12.

Figure 14:
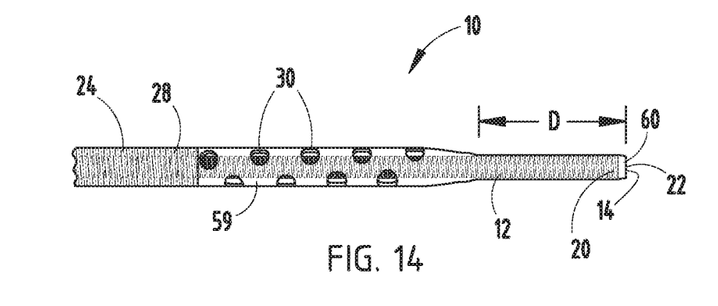
FIG. 14 is a top elevational view of another embodiment of a front portion of a coaxial cannula of the instant invention.

Referring again to FIGS. 12 and 14, the return site 60 and drainage sites 59 are separated by a distance D that provides for different amounts of mixing of oxygenated and deoxygenated blood. The distance D can vary according to the application, desired flow, and the size or maturity of the patient. FIG. 12 illustrates an extended distance D that minimizes mixing of oxygenated and deoxygenated blood during use. FIG. 14 illustrates a short distance D for use in a young patient, or for lower flow rates, or in applications where mixing of oxygenated blood and deoxygenated blood is not a critical issue.

Figures 15, 16:
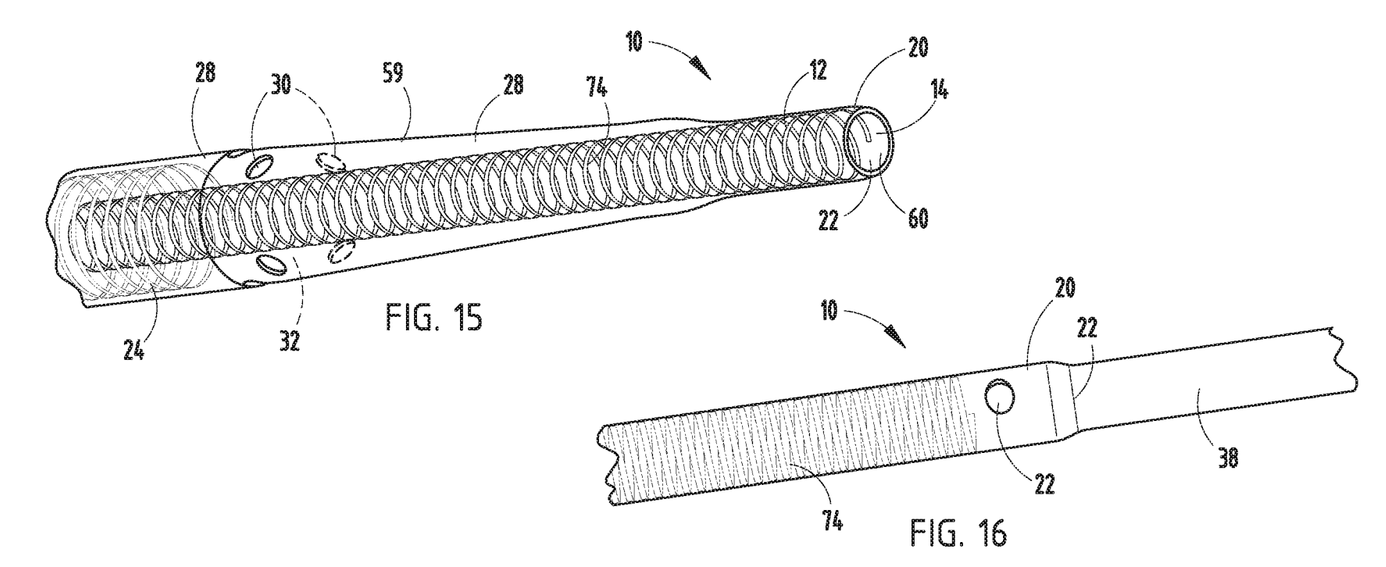
FIG. 15 is a front perspective view of the front portion of a coaxial cannula of FIG. 14.
FIG. 16 is a top elevational view of a front portion of another embodiment of a coaxial cannula of the present invention.

Referring now to FIG. 16, the return site 60 includes at least one central return aperture 22. However, it is contemplated that additional return apertures 22 may be provided that extend through the inside tube 12. The return apertures 22 may be staggered or aligned and set at various angles relative to the longitudinal extent of the inside tube 12. Additionally, a reinforcing band 61 may be installed, in the distal end 20 of the inside tube 12.

Figure 17:
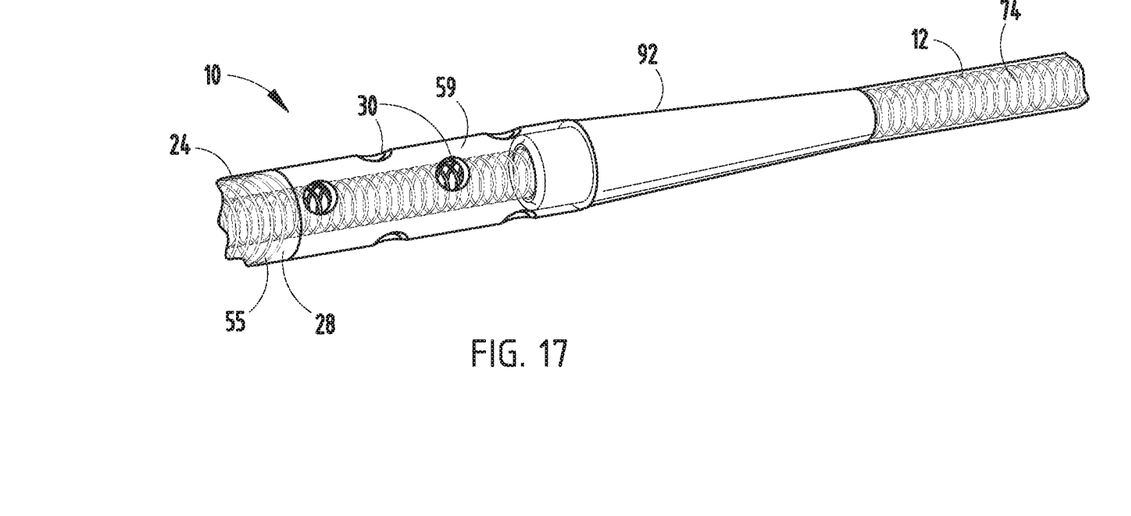
FIG. 17 is one embodiment of a transition piece of a coaxial cannula of the instant invention.

The illustrated example shown in FIG. 17, shows a transition piece 92 that provides a smooth transition from the outside wall of the inside tube 12 to the drainage site 59. If the drainage site is integral with the outside tube 24, than the transition piece 92 will abut the outside tube 24 directly. Alternatively, if a drainage member 57 is used, than the transition piece 92 will abut the forward end 58 of the drainage member 57 and taper down to and connect with the outside circumference of the inside tube 12. The transition piece 92 is adjacent to the distal end 28 of the outside tube 24 and is attached to the outside tube 24 and the inside tube 12 by adhesive or may be press fit into place.

Figure 18:
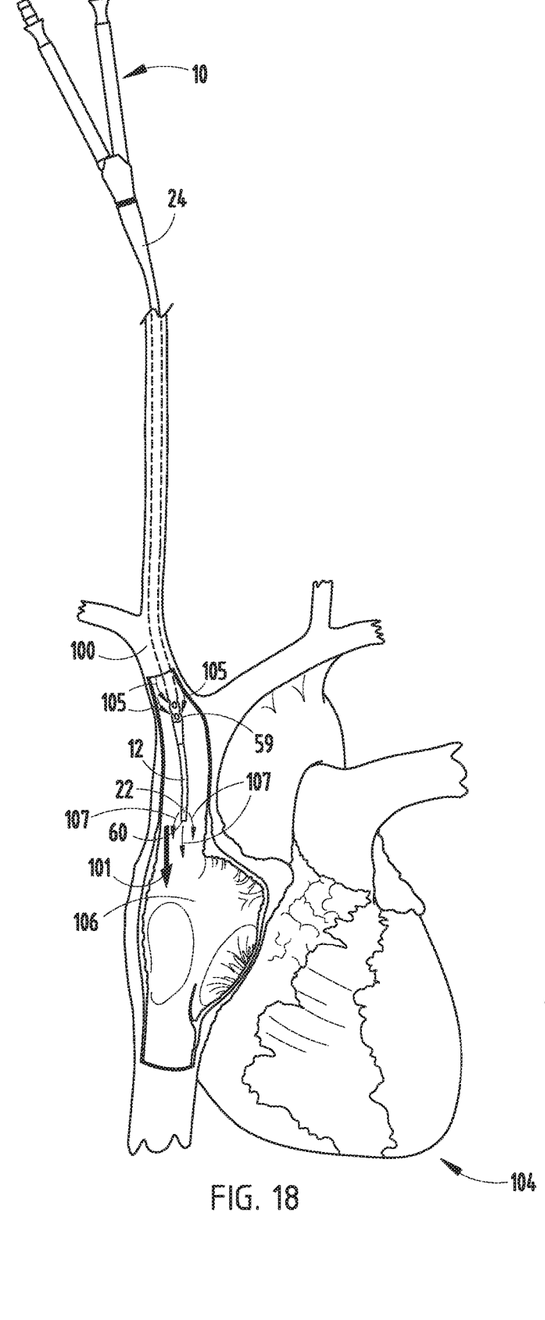
FIG. 18 is a front elevational view of a coaxial cannula of the instant invention positioned in the superior vena cava of the body of a person.
Figure 19:
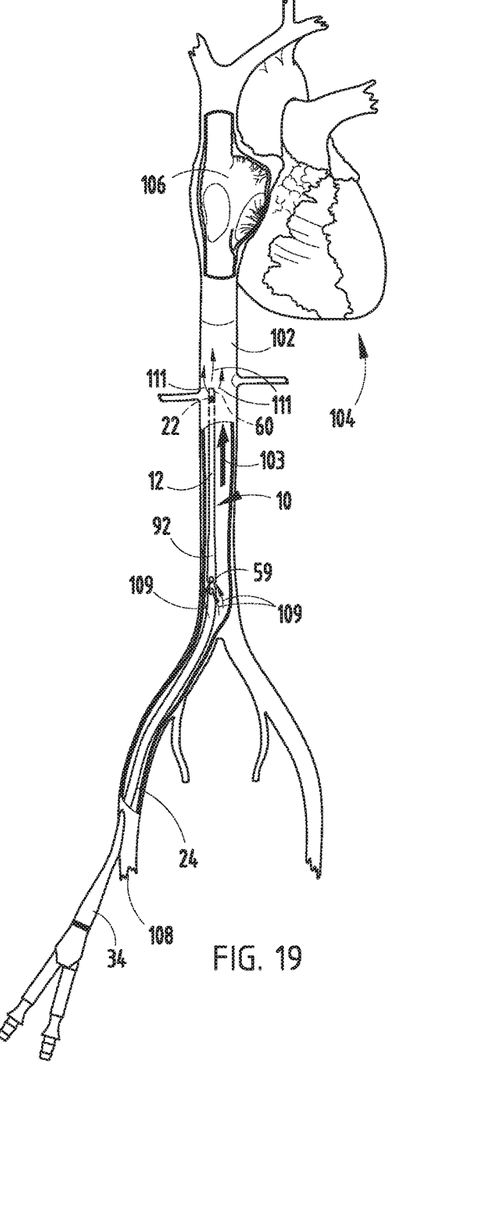
FIG. 19 is a front elevational view of a coaxial cannula of the instant invention positioned in the inferior vena cava of the body of a person.

Referring to FIGS. 18 and 19, the extracorporeal support cannula 10 can be inserted into the superior vena cava 100 or the inferior vena cava 102 of the heart 104 of the patient. The introducer 38 (FIG. 1) is provided and assists the physician in properly placing the extracorporeal support cannula 10 inside a patient's body either above the heart 104 (through the superior vena cava 100) or below the heart 104 (through the inferior vena cava 102).

As shown in FIG. 18, when the extracorporeal support cannula 10 is inserted into the superior vena cava 100, the return site 60 is located below the drainage site 59. Accordingly, as blood flows downward from the superior vena cava 100 in the direction of arrow 101 toward the right atrium 106 of the heart 104, the drainage lumen 32, by way of the drainage apertures 30, draws deoxygenated blood from the superior vena cava 100, as shown by arrows 105, and sends the blood to an ECMO unit (not shown). After the blood has been oxygenated by the oxygenator, the blood flows back through the return lumen 14 out through the return apertures 22 and into the superior vena cava 100. The blood flows back in the direction of arrows 107 into the superior vena cava 100 at the return site 60 which is positioned below and downstream of the drainage site 59. As a result, the blood flowing into the heart 104 is more oxygenated than it otherwise would be if the extracorporeal support cannula 10 was not present. Accordingly, the lungs do not need to work as hard to oxygenate the blood, because the blood is already partially oxygenated, which provides some relief to the lungs.

Alternatively, as shown in FIG. 19, the extracorporeal support cannula 10 can be inserted into the inferior vena cava 102 up through the femoral vein 108. Unlike insertion into the superior vena cava 100, the extracorporeal support cannula 10 is positioned such that the return site 60 is located above, yet still downstream of, the drainage site 59. This is possible because the inferior vena cava 102 pumps blood upwardly from the lower extremities of the body to the heart 104. As blood flows upward through the inferior vena cava 102 in the direction of arrow 103 toward the right atrium 106 of the heart 104, the drainage lumen 32, by way of the drainage aperture(s) 30, draws deoxygenated blood from the inferior vena cava 102, as indicated by arrows 109, and sends the deoxygenated blood to the ECMO unit. After the blood has been oxygenated, the blood flows back through the return lumen 14 out through the return aperture(s) 22 and into the inferior vena cava 102. As stated above, the blood flows back into the inferior vena cava 102 from the return site 60 at a position above the drainage site 59, as indicated by arrows 111. Consequently, the blood flowing into the heart 104 is more oxygenated than it otherwise would be if the extracorporeal support cannula 10 was not present. Accordingly, the lungs do not need to work as hard to oxygenate the blood, providing some relief to that organ.

In either of the applications described above (insertion through the inferior vena cava 102 or through the superior vena cava 100) as shown in FIGS. 18 and 19, the extracorporeal support cannula 10 can be used to provide partial or complete carbon dioxide removal as well as partial or complete oxygen addition. In both carbon dioxide removal as well as oxygen addition, the extracorporeal support cannula 10 can be used in long term or short term applications. The extracorporeal support cannula 10 is also designed for use in hemofiltration purposes including renal dialysis and hepatic applications. In addition, the extracorporeal support cannula 10 can be used for blood heat exchange applications to elevate or lower the temperature of the blood. These applications include hyperthermia therapy and re-warming purposes when a patient is suffering from hypothermia. The extracorporeal support cannula 10 can also be used in venovenous lung support or life support in cases where normal lung function is lessened or recovery time is required. Further, it is contemplated that extracorporeal support cannula 10 can be used in left heart (aortic) applications as well as abdominal aortic applications.

Another possible application for the extracorporeal support cannula 10 includes providing offload support to the right ventricle 110 of the heart 104. To assist the right ventricle 110 from above the heart 104, the extracorporeal support cannula 10 is first inserted through a patient's superior vena cava 100 and into the right atrium 106. The return site 60 of the extracorporeal support cannula 10 is then gently pushed through tricuspid valve 112 and into the right ventricle 114. The return site 60 is then gently eased through the pulmonary valve 116 and into the pulmonary artery 118. In this position, the drainage site 59 of the extracorporeal support cannula 10 is positioned in the superior vena cava 100 or possibly right atrium 106. Deoxygenated blood is drawn from the superior vena cava 100 or right atrium 106 as indicated by arrows 120 and oxygenated by an ECMO apparatus. The oxygenated blood is then returned to the pulmonary artery 118 through the return lumen 14 out through the return apertures 22 at the return site 60 as indicated by arrows 122, following the direction of the flow of blood, as shown by arrow 124. This positioning of the extracorporeal support cannula 10 is helpful in cases where the right ventricle 114 is not strong enough to handle full body blood volume.

Alternatively, as shown in FIG. 21, the extracorporeal support cannula 10 may be inserted into the inferior vena cava 102 and into the right atrium 106. The extracorporeal support cannula 10 is then turned to penetrate past the tricuspid valve 112 thereby entering the right ventricle 114. The return site 60 is then eased past the pulmonary valve 116 and into the pulmonary artery 118. As deoxygenated blood flows up from the inferior vena cava 102 into the right atrium 106, deoxygenated blood is drained from the inferior vena cava 102 or right atrium 106 and oxygenated in an ECMO apparatus, as indicated by arrows 126. The oxygenated blood is then returned to the pulmonary artery 118 through the return apertures 22 of the return site 60, as shown by arrows 128, following the direction of the flow of blood designated by arrow 124.

The above description is considered that of the preferred embodiments only. Modifications of the invention will occur to those skilled in the art and to those who make or use the invention. Therefore, it is understood that the embodiments shown in the drawings and described above is merely for illustrative purposes and not intended to limit the scope of the invention, which is defined by the following claims as interpreted according to the principles of patent law, including the Doctrine of Equivalents.

What is claimed is:

1. A method of making a cannula assembly, the method comprising:
   forming an elongate flexible infusion tube having a proximal end and a distal end;
   forming an elongate flexible drainage tube having a proximal end and a distal end;
   forming a connector having a return opening and a connector aperture;
   inserting said elongate infusion tube into said return opening and out said connector aperture such that a portion of said infusion tube extends through said connector, wherein said portion of said infusion tube extending through said connector gradually tapers across said connector;

attaching said infusion tube to said return opening of said connector;

connecting said distal end of said elongate drainage tube to a mid-portion of said elongate infusion tube;

installing a drainage site having at least one drainage aperture at said distal end of said elongate drainage tube; and installing an infusion site having at least one infusion aperture at said distal end of said elongate infusion tube.

2. The method of claim 1, further comprising installing a reinforcing coil in a wall of said drainage tube.

3. The method of claim 1, further comprising installing a reinforcing coil in a wall of said infusion tube.

4. The method of claim 1, further comprising installing a reservoir in said connector fluidly connected to a mouth on said drainage tube.

5. The method of claim 4, wherein said reservoir receives fluid from said proximal end of said drainage tube.

6. The method of claim 1, further comprising:
attaching an outer surface of said infusion tube to said return opening of said connector in the attaching step;
connecting a drainage member to said distal end of said drainage tube and to said outer surface of said infusion tube between said proximal end and said distal end of said infusion tube, said drainage member including said at least one drainage aperture; and
attaching a first end of said drainage member to said distal end of said drainage tube and attaching a second end of said drainage member to said outer surface of said infusion tube.

7. The method of claim 2, wherein said reinforcing coil installed in said wall of said drainage tube extends from said proximal end of said drainage tube to said distal end of said drainage tube.

8. The method of claim 3, wherein said reinforcing coil installed in said wall of said infusion tube extends from said proximal end of said infusion tube to said distal end of said infusion tube.

9. The method of claim 1, wherein a diameter of said proximal end of said infusion tube is greater than a diameter of a body portion of said infusion tube.

10. The method of claim 1, wherein said drainage tube is co-axially aligned with said infusion tube, said infusion tube remaining substantially coaxial with said drainage tube throughout a length of said drainage tube and said length of said drainage tube being less than a length of said infusion tube.

11. The method of claim 1, wherein said connector aperture is fluidly connected to said proximal end of said drainage tube.

12. A method of making a cannula assembly, the method comprising:

inserting an elongate flexible infusion tube into a return opening of a connector and out a connector aperture of said connector such that a portion of said infusion tube extends through said connector, wherein said portion of said infusion tube extending through said connector gradually tapers across said connector, and wherein a distal end of said infusion tube has an infusion site defining at least one infusion aperture;

attaching said infusion tube to said return opening of said connector; and connecting a distal end of an elongate drainage tube to a mid-portion of said elongate infusion tube, said distal end of said elongate drainage tube having a drainage site defining at least one drainage aperture at said distal end of said elongate drainage tube.

13. The method of claim 12, further comprising installing a reinforcing coil in a wall of said drainage tube, said reinforcing coil installed in said wall of said drainage tube extending from a proximal end of said drainage tube to said distal end of said drainage tube.

14. The method of claim 12, further comprising installing a reinforcing coil in a wall of said infusion tube, said reinforcing coil installed in said wall of said infusion tube extending from a proximal end of said infusion tube to said distal end of said infusion tube.

15. The method of claim 12, further comprising installing a reservoir in said connector fluidly connected to a mouth on said drainage tube.

16. The method of claim 15, wherein said reservoir receives fluid from a proximal end of said drainage tube.

17. The method of claim 12, further comprising:
attaching an outer surface of said infusion tube to said return opening of said connector in the attaching step;
connecting a drainage member to said distal end of said drainage tube and to said outer surface of said infusion tube between a proximal end and said distal end of said infusion tube, said drainage member including said at least one drainage aperture; and
attaching a first end of said drainage member to said distal end of said drainage tube and attaching a second end of said drainage member to said outer surface of said infusion tube.

18. The method of claim 12, wherein a diameter of a proximal end of said infusion tube is greater than a diameter of a body portion of said infusion tube.

19. The method of claim 12, wherein said drainage tube is co-axially aligned with said infusion tube, said infusion tube remaining substantially coaxial with said drainage tube throughout a length of said drainage tube and said length of said drainage tube being less than a length of said infusion tube.

20. The method of claim 12, wherein said connector aperture is fluidly connected to a proximal end of said drainage tube.

\* \* \* \* \*